United States Patent
Oudovikine

(10) Patent No.: US 9,372,075 B2
(45) Date of Patent: Jun. 21, 2016

(54) SYSTEM AND METHOD FOR FATIGUE FORECASTING AND STRAIN MEASUREMENT USING INTEGRAL STRAIN GAUGE (ISG)

(75) Inventor: Alexandre Oudovikine, Maple (CA)

(73) Assignee: PARADIGM SHIFT TECHNOLOGIES INC., Toronto (CA)

( * ) Notice: Subject to any disclaimer, the term of this patent is extended or adjusted under 35 U.S.C. 154(b) by 0 days.

(21) Appl. No.: 12/786,875

(22) Filed: May 25, 2010

(65) Prior Publication Data

US 2010/0299086 A1 Nov. 25, 2010

Related U.S. Application Data

(63) Continuation of application No. 11/875,206, filed on Oct. 19, 2007, now abandoned.

(60) Provisional application No. 60/859,957, filed on Nov. 20, 2006.

(51) Int. Cl.
*G01L 1/00* (2006.01)
*G01B 11/16* (2006.01)
*G01N 3/32* (2006.01)

(52) U.S. Cl.
CPC . *G01B 11/16* (2013.01); *G01N 3/32* (2013.01)

(58) Field of Classification Search
CPC .................................. G01B 11/16; G01N 3/32
USPC ............ 702/42; 73/784, 24.06, 862.622, 594, 73/600, 774, 800, 787; 600/594; 482/143; 385/12
See application file for complete search history.

(56) References Cited

U.S. PATENT DOCUMENTS

| | | | | |
|---|---|---|---|---|
| 1,906,803 | A | * | 5/1933 | Mueller .................... 359/291 |
| 2,294,897 | A | | 9/1942 | Ellis |
| 3,005,332 | A | | 10/1961 | McClintock |
| 3,433,060 | A | * | 3/1969 | Rastogi et al. .................. 73/774 |
| 3,715,915 | A | | 2/1973 | Williams |
| 3,979,949 | A | * | 9/1976 | Smith ............................. 73/787 |
| 4,015,465 | A | * | 4/1977 | Scott ............................... 73/800 |
| 4,179,940 | A | | 12/1979 | Oertle et al. |
| 4,265,120 | A | * | 5/1981 | Morris et al. .................. 73/600 |
| 4,625,567 | A | * | 12/1986 | Frayer et al. ............. 73/862.041 |
| 4,869,113 | A | | 9/1989 | Sarrazin |
| 5,018,389 | A | * | 5/1991 | Mraz ............................... 73/784 |

(Continued)

FOREIGN PATENT DOCUMENTS

WO WO2006/112152 10/2006

OTHER PUBLICATIONS

Bennet et al., Introduction to Surface Roughness and Scattering, 2nd Edition, Optical Society of America, 1999, ISBN/ISSN: 1557526095.*

(Continued)

*Primary Examiner* — Tung S Lau
*Assistant Examiner* — Xiuquin Sun
(74) *Attorney, Agent, or Firm* — Lathrop & Gage LLP

(57) ABSTRACT

The present invention relates to means, system and method for measurement of stress strain and fatigue forecasting by the means of Integral Strain Gauges (ISGs) capable of recording information from a surface of a tested object, mathematical processor for analysis of the information recorded on the surface of such gauges. Integral Strain Gauges produced from a custom made reaction sensitive materials.

6 Claims, 6 Drawing Sheets

(56) References Cited

U.S. PATENT DOCUMENTS

| | | | |
|---|---|---|---|
| 5,531,123 A | 7/1996 | Henkel | |
| 6,240,783 B1 * | 6/2001 | McGugin et al. | 73/594 |
| 6,592,502 B1 * | 7/2003 | Phillips | 482/143 |
| 6,778,236 B1 * | 8/2004 | Crawford | G01B 11/165 33/501 |
| 7,181,959 B2 * | 2/2007 | Matsumoto et al. | 73/114.01 |
| 7,299,678 B2 * | 11/2007 | Atherton | 73/24.06 |
| 7,515,781 B2 * | 4/2009 | Chimenti et al. | 385/12 |
| 8,082,799 B2 | 12/2011 | Oudovikine | |
| 2005/0273277 A1 * | 12/2005 | Ridnour et al. | 702/42 |
| 2007/0276294 A1 * | 11/2007 | Gupta et al. | 600/594 |
| 2009/0013762 A1 | 1/2009 | Asahina et al. | |
| 2010/0064819 A1 | 3/2010 | Oudovikine | |

OTHER PUBLICATIONS

International Search Report for PCT/CA2007/001893 Mailed Feb. 7, 2008.

Written Opinion for PCT/CA2007/001893 Mailed Feb. 7, 2008.

International Preliminary Report on Patentability for PCT/CA2007/001893 Mailed Mar. 19, 2009.

Office Action and response corresponding to U.S. Appl. No. 12/515,698, Office Action mailed Feb. 17, 2011.

* cited by examiner

TOP VIEW

SIDE VIEW

SYSTEM AND METHOD FOR FATIGUE FORECASTING AND STRAIN MEASUREMENT USING INTEGRAL STRAIN GAUGE (ISG)

CROSS-REFERENCE TO RELATED APPLICATIONS

This application is a continuation application of U.S. application Ser. No. 11/875,206 filed Oct. 19, 2007, now abandoned, which claims the benefit of U.S. provisional application Ser. No. 60/859,957 filed Nov. 20, 2006. U.S. application Ser. No. 11/875,206 is hereby incorporated by reference in its entirety to the extent not inconsistent with the disclosure herein.

FIELD OF THE INVENTION

Stress measurement and fatigue forecasting system of the present invention introduces a new revolutionary approach in a field of applied physics and chemistry, and more particularly in material science.

PRIOR ART

The measurement of stress-strain and fatigue conditions within a test object, such as a structural or mechanical element, has commonly been achieved using electrical (conventional) strain gauges. The major area of application of these gauges is a measurement of stress-strain values in static loading conditions. The principle of action of electrical gauges can be characterized as a differential type. This type of gauges reacts to a single cycle of loading and their reaction (resistance) correlates with a single parameter of loading, stress level S. Electrical strain gauges react only in a process of loading and after unloading the reaction disappears. It means those kind of gauges can not be used for cyclic loading and can not accumulate reaction and consequently the "history of loading" during some term of cyclic loading.

Electrical gauges sizes allow to measure average stress level according classical theoretical dependence:

$S=F/A;$

Where: S-stress value; F-force; A-area of cross section.

This approach does not consider microstructure (for example crystalline structure of metals) of real material therefore electrical gauges do not allow to measure stress value on the micro level (this stress value is responsible for material destruction), for example between crystalline grains of metals.

Electrical strain gauges do not react on the micro defects, micro irregularities of tested materials and roughness of a surface.

Electrical strain gauges have electrical wires, connectors and switches and for this reason can not be used in access challenged locations (such as on the satellites or gear boxes).

SUMMARY OF THE INVENTION

Integral Strain Gauges (ISGs) are made from a wide variety of a custom made materials by a wide variety of methods, such as electroplating, or other deposition methods, plastic rolling with following machining and chemical processing.

Chemical composition and mechanical properties of ISGs result in creation of a sensitive plane of such gauges capable of recording delicate changes of parts subjected to testing.

ISGs are generally attached to a surface of tested elements. Such elements are subjected to multiple types of testing loads depending on the purpose of the experiment. Reactions to such loads, among most commonly known ones to be classified as static strain loads and cyclic or so called repetitive loads are properly recorded by ISGs. Depending on the nature of trials, information recorded on ISGs can be retrieved through a number of loading cycles having a gauge detached for the convenience of the reaction analysis. Alternatively, depending on the final purpose of a test, ISGs can be attached on the testing element through out its entire lifetime having the reaction readings recorded in specified intervals. Reaction readings and processing can be attained by means of a mathematical processor programmed specifically to perform such calculations.

ISGs of the present invention have ability "to remember" the history of loading and accumulate the machine part fatigue events. This feature, similar to a concept of a "black box" on airplanes, allows analysis of structural damage or destruction of a tested part over a period of exploitation or predefined testing time.

Under the influence of cyclic loads or cyclic strains the internal reaction of the ISG changes and the outward effect appears on the surface of the gauge whereas the magnitude of the changes of the reaction pertaining to repetitive loads correlates with a number of cycles of the amplitude of a cyclic deformation.

ISGs of the present invention have a number of attributes pertaining their internal composition and structure including type of materials, multi layer formation and shapes. Additionally, ISGs can be classified as having isotropic or non-isotropic properties (identical or not identical structure in all directions). Regardless of the positioning of a non-isotropic version of an Integral Strain Gauge relative to the forces of strain applied upon the tested element, proper reaction is recorded by the gauge during the testing cycle. ISGs of an isotropic kind, typically record the reaction along lines of their mechanical composition.

Typical usage cycle of the present invention comprises classical calibration—testing model. First stage relates to calibration of ISGs and building of the γ–N (amplitude of cyclic deformation—number of cycles for a different grade of ISG reaction) dependency curve which is followed by second stage of testing. Calibration dependency may also be established using unique mathematical methods applicable to a specific situation.

Fatigue forecasting of the present invention is performed once establishing correlations between ISG calibration curves and fatigue curves.

Let us now introduce a specific embodiment. It should be understood that various modifications and adaptations of such embodiment can be made without departing from the present invention.

DESCRIPTION OF A SPECIFIC EMBODIMENT

Figure 1:
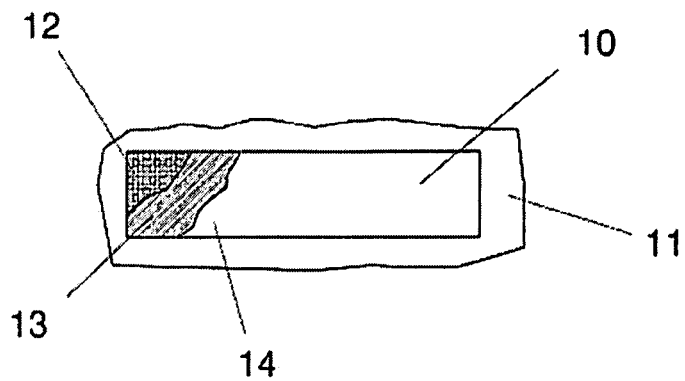
FIG. 1 Three layers of an ISG, top view.

The first embodiment of the invention will now be explained by referring to FIG. 1, which depicts an internal structure of a particular version of an Integral Strain Gauge (ISG) for measuring and determining the stress-strain conditions and forecasting of a life time duration within a test object. ISG (10) is designed to enable a tester to measure the deformation when the Integral Strain Gauge (10) is applied to the test object (11) and thereby be used to approximate the fatigue, capacity and expected working life span of the test element (11).

During the testing stage, ISGs are attached to a surface of tested elements that subjected to a strain load and the reaction captured on such gauges is recorded appropriately.

Figure 2:
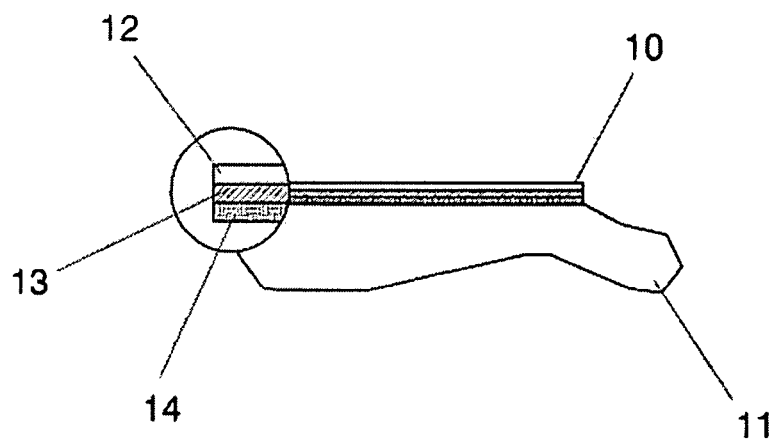
FIG. 2 Three layers of an ISG, side view.

Sensitivity of ISG's surfaces is dependant on the internal structure of its composition, creating a unique capacity of recording the reaction reflecting changes of the deformation of the tested materials based on a variety of factors such as reflection ability, size and density of grains, micro hardness, physical and chemical properties etc. Referring to FIG. 2, levels (12), (13), (14) existing on the ISG depicted for the purpose of description of the present embodiment.

Method of usage of ISGs can be further summarized in a number of consecutive stages.

Stage I. Calibration Test of a Particular Type of an ISG.

Calibration procedure is typically performed in a number of consecutive steps that begin with attachment of the ISG on a surface of a calibrating specimen. Such process can be performed by application of suitable adhesives or any other means of attachment. Upon completion, tested samples are loaded by a number of stress levels $S_1, S_2, S_3 \ldots S_n$. While loading such specimen, tests are interrupted after a predetermined number of testing cycles $N_1, N_2, N_3 \ldots N_n$, and the reaction pertaining each set is recorded accordingly. Based on the recorded information, calibration dependency curve is built in coordinates S-N (for different grade of ISG reaction R) using a mathematical equation or proximity of the data established during experimental process of a present stage.

Stage II. Creation of a Fatigue Curve.

Fatigue curve is typically built based on results of a fatigue testing of samples. Said samples are usually prepared from a material similar to that of a tested element. Technological process of creation of such sample it typically analogous to that of the tested element. Fatigue test can be performed on the real structural part as well.

Fatigue testing likewise testing performed for the establishment of the calibration dependency can be completed having various types of strain, such as a strain of twisting, stretching, bending or a composite of such depending on best proximity to the simulation of actual occurrence of the load.

Similar to the stage of calibration, reaction of the tested sample is obtained using ISG attached it the surface whereas number of cycles till the destruction of the tested sample is recorded. Such testing is conducted at various levels of strain for completion of the required sets of the experimental data. Accuracy of fatigue curve is typically dependant on the completeness of the data and larger array of levels of strain selected for the testing purposes. Additionally, such curve can be further described using mathematical equations.

Stage III. Life Time Prediction.

Following previously described stages, ISGs are attached on the surface of tested element subjected to a strain loading conditions. Such loading is interrupted after a predetermined number of cycles and the point of maximum reaction of strain is recorded. Using calibration dependency received previously curve corresponding to the intense reaction, corresponding to the maximum stress level of the present test is expressed. Such expression can be later resolved for a level of magnitude of acting strains on a micro-level which would allow calculation of the number of cycles prior to destruction once employing the fatigue curve of stage II.

STATEMENT OF OPERATION

Stage I. Calibration test of a particular type of an ISG. As an example of an application of the methodology of the present invention, let us describe calibration stage of an ISG of a conical specimen (15) as shown on FIG. 6 being subjected to a twisting strain applied by a testing machine following arrows (16).

Figure 9:
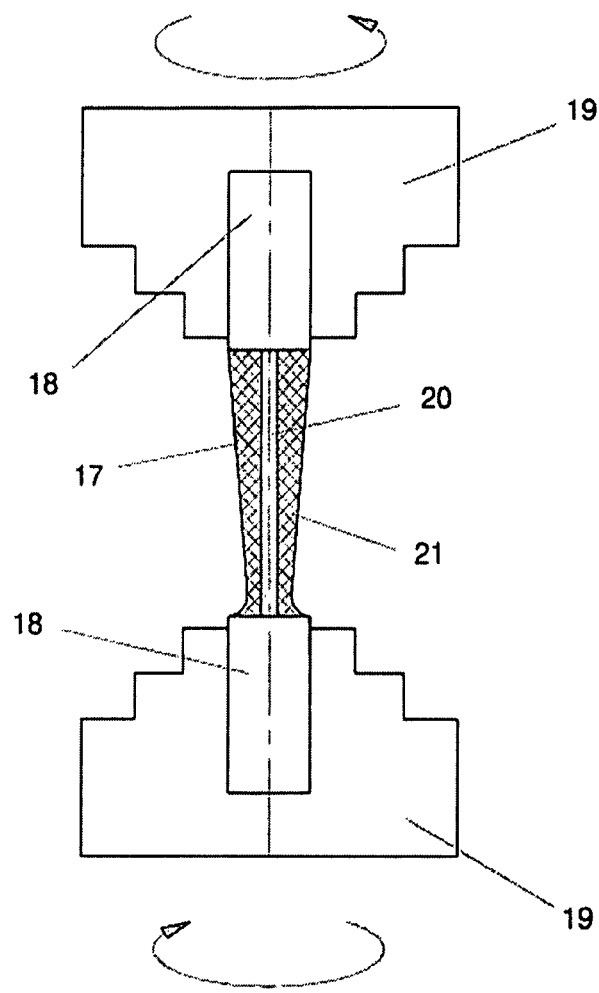
FIG. 9 Calibration specimen.

Let us now describe the structure of a specimen depicted in further detail on FIG. 9. It was recognized that the true nature of tested materials, such as metals though commonly considered as a monolithic matter, rarely if ever behave as per commonly perceived patterns.

Tested specimen of FIG. 9 comprises a conical shaft (17), cappings (18) located on opposite edges of the shaft and provided for the purpose of fixation of the said shaft in spindles (19) of a testing machine. Internally, conical shaft consists of a double layer structure, namely inner rod (20) and the outer working shell (21). Outer working shell (21) is assigned for attachment of gauges undergoing stage of calibration.

Inner rod of the specimen is comprised of a durable metal. Outer working shell (21) is composed of an amorphous material such as plastic. Outer shell is attached firmly to the inner rod.

Thus, present specimen comprises a solid object composed of two types of materials.

Calibration stage of the test described herein facilitated by creation of calibration dependency γ–N (when $R_1$=const, $R_2$=const, $R_3$=const . . . Rn=const) for an ISG where composite calibration specimens are utilized through a predetermined number of testing cycles.

Figure 6:
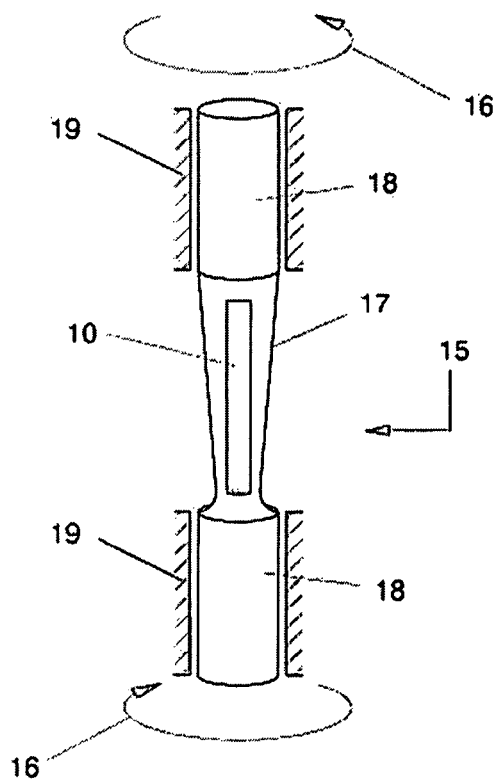
FIG. 6 ISG applied on a conical sample.

As shown on FIG. 6, ISG gauge (10) is fixed on the surface of the conical specimen (15) by means of a reaction sensitive adhesive. Conical structure (17) of such specimen creates a condition of coverage of the specimen at various radiuses on the surface of application.

Figure 5:
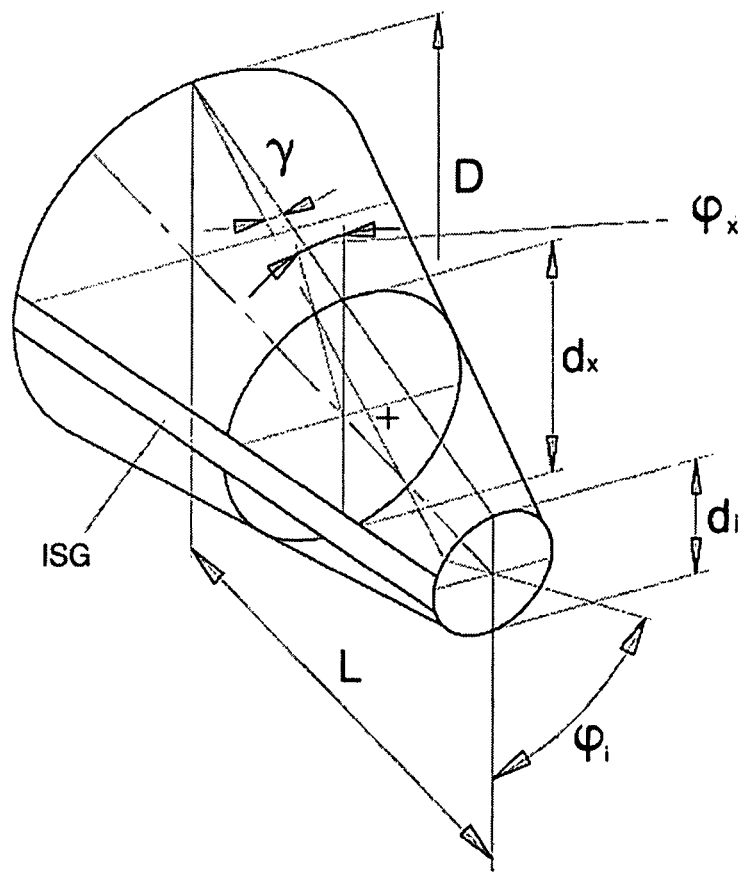
FIG. 5 Conical sample subjected to a twisting strain, variables used for establishment of a calibration dependency.

Specimen is fixed in spindles (19) and subjected to cyclic strain (twisting) with constant amplitude of twisting ($\lambda_a$=const; where $\lambda_a$ is the angle of twist). For a purpose of achieving precision dependency readings, amplitude of deformation of the sample is maintained constant through out the entire stage of a testing stage. Such procedure is interrupted after $N_1, N_2, N_3 \ldots N_i$ loading cycles or predefined periods of time for the purpose of reading of integral characteristics of the reaction from the surface of the ISG by the means of a scanner device. Referring to FIG. 5, we can further calculate the dependency of:

$$\gamma_x = \frac{\lambda_i * 3D^3 * d_i^3}{2dx^3 L(D^2 + d_i D + d_i^2)}. \quad \text{Equation 1}$$

Upon completion, received is a set of data where i—is a number of pair of values ($N_i \Sigma R_i$) where $N_i$—is the number of loading cycles after the $i^{th}$ interrupt;

$\Sigma R_i$—is the integral characteristic of the reaction of the ISG and the extent of distribution of the reaction and micro-shear deformation on a surface of the ISG and the sample accordingly.

Figure 8:
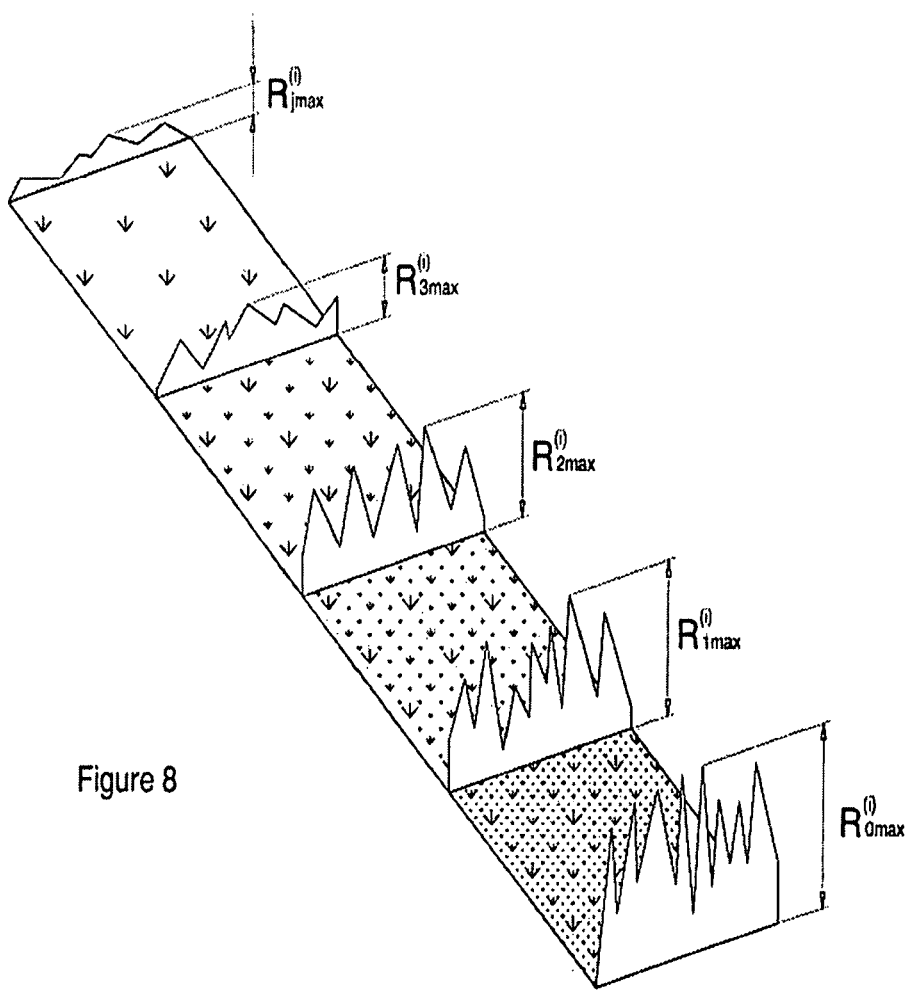
FIG. 8 Reaction of a maximum intensity $R_{Nmax}$ recorded on a surface of the ISG.

Additionally, in various sections of the specimen with diameters $d_0, d_1 d_2, \ldots d_j$, points of maximum intensity of reaction $R_{0Max}, R_{1Max}, R_{2Max}, \ldots R_{JMax}$ are identified and recorded for the purpose of subsequent calculation. Points of maximum reaction intensity are shown on of FIG. 8.

Based on Equation 1, described herein, and additional mathematical dependencies well known in the art, it is now possible to calculate the value of shear deformation $\gamma$ and later the tangential stress $\tau$ for a particular material having known module of displacement G.

All of the data is received in an experimental (R,N) and computational ($\gamma,\tau$)approach allows building of calibration dependency curve for a particular type of an ISG.

Figure 3:
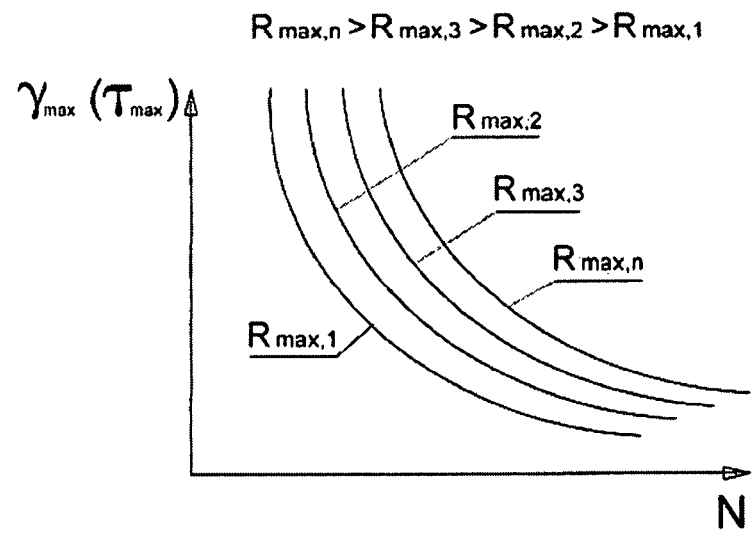
FIG. 3 Set of curves representing calibration dependency of a particular ISG type.

Let us now refer to FIG. 3, where:

In coordinates $\gamma_{Max}(\tau_{Max})$–N is described a number of curves each of which is built having $R_{Max}$=const.

Each of the curves in coordinates $\tau_{Max}$–N represents characteristics of level of fatigue damage and thus can be described by a mathematical dependency:

$$N = K\left[\frac{1}{\tau_{Max} - D*C} - \frac{c_1}{\tau_{Max}(c_1 - DC)}\right]. \quad \text{Equation 2}$$

Where:

N—number of cycles of the corresponding ISG reaction;

$\tau_{Max}$—amplitude of tangential stress;

D—level of fatigue damage of the tested element material which corresponds to the ISG reaction R;

C, $c_1$, K—constants of the equation.

Thus set of curves of FIG. 3, in coordinates $\tau$–N can be accurately described by a set of equations similar to that of Equation 2.

Stage II. Creation of a Fatigue Curve.

Let us now describe the second stage of the methodology of the present invention namely fatigue testing and creation of a fatigue curve. The fatigue test can be performed on samples with shape similar to the calibrating specimen (15) of FIG. 6, but manufactured of the same material and technology as a real structural part or on the real tested element. In the present description, twisting strain similar to that of a strain applied in stage I is acting upon specimen of FIG. 6.

Prior to beginning of the fatigue testing, an ISG is attached to the surface of tested element, fixed in spindles of a test rig and subjected to cyclic strain.

Tested element is subjected to the said strain according to the methodology of the present invention until an appearance of the reaction on the ISGs attached to the tested samples on multiple levels of strain $\tau_1, \tau_2, \tau_3 \ldots \tau_j$. Through out the process, the fatigue testing is interrupted predetermined number of times corresponding to a number of cycles $N_1, N_2, N_3 \ldots N_j$. Following every interrupt occurrence, reaction $\Sigma R$ from the surface of the ISGs is read by the means of a scanning device. All of the data is properly recorded for the purpose of further analysis.

Though out the process, said testing procedures are continued until the finite destruction of samples for each level of strain $\tau$. Numbers of cycles elapsed till sample destruction $N_f$ is recorded accordingly for every level.

Following, each value of integral characteristic of $\Sigma R$ identified and analyzed. Recorded are those points ISG having maximum intensity of reaction.

Using sets of data of present experiments in conjunction with values of calibration dependency ($\gamma$–N) received previously, maximum values of shear deformation ($\gamma_{Max}$) corresponding to maximum level of intensity of ISG reaction $R_{max}$ for all values of present strain ($\tau_j$) and number of cycles ($N_i$) are calculated. Shear deformation ($\gamma_{Max}$) is subsequently recalculated into tangential stress ($\tau_{Max}$) and is recorded appropriately.

Figure 7:
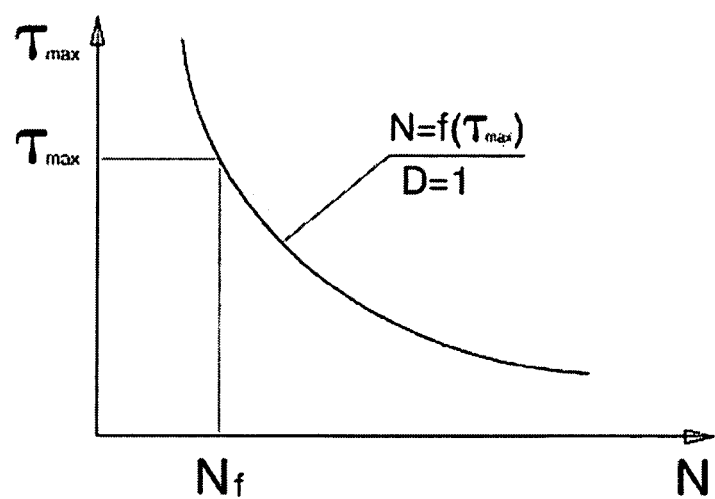
FIG. 7 Fatigue curve.

Such data allows us to build the fatigue curve in coordinates of $\gamma_{Max}$–N or $\tau_{Max}$–N as shown on FIG. 7 having D=1.

Fatigue curve received in such method can be described in a similar mathematical dependency as the calibration dependency in coordinates ($\tau_{Max}$–N) having D=1.

$$N_f = K\left[\frac{1}{\tau_{Max} - C} - \frac{C_1}{\tau_{Max}(C_1 - C)}\right]. \quad \text{Equation 3}$$

Where:

$N_f$—is a number of cycles of loading preceding destruction of the sample;

$\tau_{Max}$—real magnitude of micro-level strains;

K, C, $C_1$—constant parameters received throughout the stage of calibration dependency.

Stage III. Life Time Prediction.

Completing calibration dependency and fatigue testing stages final stage may begin. Approach to this stage is dependant on type of a strain applied against the tested object where 3 major conditions may occur:

1. Level of strain is constant and the number of loading cycles can be predetermined;
2. Level of strain is changing according to a set block of loads where the number of block phases is predetermined;
3. Level of strain and the corresponding number of cycles is changing in random.

Let us now describe specifics of testing applicable to 3 major conditions of strain occurrences.

Figure 4:
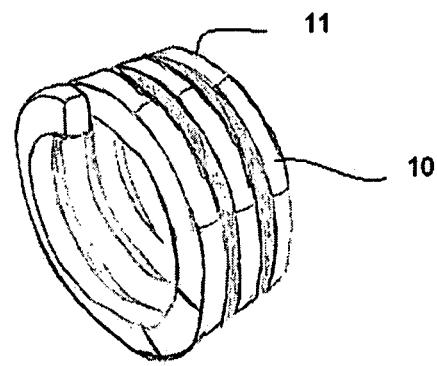
FIG. 4 Tested element (spring) with ISGs attached.

1. Under the first condition, through out exploitation of the element, the value of cyclic load such as, torque amplitude ($T_a$) is a constant value and the number of cycles can be defined precisely. Referring now to FIG. 4, ISG (24) is attached to the tested object (26) and subject it to a strain load till the reaction $\Sigma R$ appears on the surface of the ISG. Number of cycles of loading preceding appearance of such reaction is as well as the point of maximum reaction intensity $R_{max}$ that corresponds with the maximum local strain $\tau_{Max}$ are recorded.

On the calibration dependency in coordinates ($\tau_{Max}$–N) found are the curve that corresponds to the reaction $R_{Max}$ and mathematical dependency for such a curve:

$$N_f = K\left[\frac{1}{\tau_{Max} - DC} - \frac{c_1}{\tau_{Max}(c_1 - DC)}\right]. \quad \text{Equation 4}$$

Where:

$\tau_{Max}$—amplitude of tangential stress;

K, C, $c_1$—constants of the present equation;

D—level of fatigue damage of the tested element material which corresponds to the ISG reaction R;

$N_f$—is a number of cycles of loading preceding destruction of the sample;

Substituting in to Equation 4 number of cycles of loading N, $\tau_{max}$ can be calculated.

As a final point of the present stage, calculation of number of cycles of loading till the destruction of the element can be derived substituting the value of $\tau_{max}$ in to the equation of the fatigue curve (Equation 3) and resolved with respect to parameter $N_f$.

2. Under the second condition, through out exploitation of the tested element, the value of cyclic load such as, strain level is changing according to a set block of loads where the number of block stages is predetermined. Such condition can be further described using following variables:

$t_i$—duration of the testing on the $i^{th}$ stage of a block load;
$g_i=\tau_i/\tau_{Max}$—is a level of strain on the $i^{th}$ stage of a block load.

Similar to the first condition, an ISG is attached on a surface of a tested element and reaction $R_{Max}$ following N cycles of loading is recorded. For the purpose of this calculation, the number of cycles N corresponds to a whole number of block phases. Such reaction $R_{Max}$ corresponding to the reaction $R_{Max2}$ of the calibration dependency having all of parameters defined (K, $D_j$, $c_1$C). Occurrence of the reaction $R_{Max}$ shows that following N cycles of block load, damage value of D on the surface of the ISG corresponds to the reaction $R_{Max}$. Thus we can further describe dependencies for a block load condition as following:

$$N = \frac{N_i}{t_i}; N = \sum_{i=1}^{m} N_i;$$

Where:
$N_i$—is the duration of the testing on the $it^{th}$ stage;
m—is a number of sages of a single block load.

Following dependencies can be described for a 3 stage loading block:

$$D = D_1 + D_2 + D_3$$

$$R_{Max} = R_{Max1} + R_{Max2} + R_{Max3}$$

Where:
$D_1$; $D_2$; $D_3$—is the damage on a surface of the ISG accumulated after every subsequent stage of a block load;
$R_{Max1}$; $R_{Max2}$; $R_{Max3}$—reaction on the ISG recorded after each subsequent stage of a block load.

Based on dependencies described above, value of the maximum equivalent strain ($\tau_{Max.e}$) is derived based on the following equation:

$$N = K\left[\frac{1}{\tau_{Max.e} - DC} - \frac{c_1}{\tau_{Max.e}(c_1 - DC)}\right]. \quad \text{Equation 5}$$

Where:
N is a number of cycles of a block load;
K, D, C, $c_1$—constants of the present equation of the calibration dependency;
($\tau_{max.e}$)—a value of the maximum equivalent strain Equation 5 is resolved for $\tau_{max.e}$ which is substituted into the equation 3 for derivation of $N_f$, number of cycles of loading preceding destruction of the tested element.

3. Under the third condition, through out exploitation of the tested element, the value of cyclic load such as strain level is randomly changing. Number of cycles loading is not defined for this type of a condition.

Similar to the second condition, solution to the problem is based on the appearance of ISG reaction of a similar intensity that correlates to a corresponding level of a damage of the tested element.

Thus we can infer further relevance of strain value of ($\tau_{max.e}$) and equivalent number of lading cycles ($N_E$) based on the amount of a damage effect.

We can now suggest 2 distinct problem solutions.

Solution I. This method is based on usage of ISGs of a variable sensitivity to values of cyclic deformations. Calibration dependencies ($\tau$–N) for said gauges established accordingly.

Testing of elements with ISGs ($ISG_1$,$ISG_2$) conducted until the appearance of a reaction of a similar intensity such as $R_{Max2}$ where the duration of the testing $t_1$ for $ISG_1$ and the duration $t_2$ for $ISG_2$ are recorded accordingly.

In such setup, equivalent cycle numbers for ISGs $N_{E1}$ $N_{E2}$ can be defined as:

$$N_{E1} = t_1 * K_E; N_{E2} = t_2 * K_E$$

Where:
$K_E$—is the coefficient of equivalency correlating to a cycle/duration ratio.

Based on such dependencies, following system of equations can be derived:

$$N_{E1} = K_E * t_1 = K\left[\frac{1}{\tau_{Maxe} - D_1 C} - \frac{c_1}{\tau_{Maxe}(c_1 - D_1 C)}\right] \quad \text{Equation 6}$$

$$N_{E2} = K_E * t_2 = K\left[\frac{1}{\tau_{Maxe} - D_2 C} - \frac{c_2}{\tau_{Maxe}(c_2 - D_2 C)}\right].$$

Solving this system of equations allows deriving values of ($\tau_{Max.e}$), and $K_E$, and subsequently $N_{E1}$,$N_{E2}$.

Following, substituting of ($\tau_{max.e}$) into the equation of the fatigue curve (Equation 3) is resolved with respect to parameter $N_f$ which can be measured in units of equivalent cycles $N_{fE}$ or timing $t_f$.

Solution II. This method is based on usage of ISGs of a uniform sensitivity. In this method, for computation of equivalent strains ($\tau_{Maxe}$) coefficient of equivalency $K_E$ of calibration dependencies received for different criteria of reaction of a similar type of ISGs such as $R_{Max1}$, $R_{Max2}$.

Following method of determining equivalent parameters $\tau_{Maxe}$, $K_E$, $K_E$, $N_{E2}$, as well as resolution with respect to $N_{fE}$ is similar to that described in Solution I.

I claim:

1. A method for using an integral strain gauge (ISG) to predict the lifetime of a test object, the surface of the ISG comprising a reaction sensitive material, the surface of the reaction sensitive material indicating a reaction due to a change in grain size and number of grains per unit area at the surface of the reaction sensitive material upon deformation of the attached test object, the method comprising the steps of:
   a) attaching the ISG to the surface of the test object;
   b) applying a plurality of loading cycles to the test object, the number of loading cycles being known and the loading cycles inducing cyclic strain in the test object, with the amplitude of the loading induced strain being constant;
   c) reading a reaction value on the surface of the ISG attached to the test object;
   d) determining the maximum stress or loading induced strain during step b) from the ISG reaction value of step c) and a predetermined relationship between ISG reaction value, amplitude of tangential stress or shear deformation and number of loading cycles;

e) determining the number of cycles to failure from the maximum stress or loading induced strain determined in step d) and a predetermined relationship between number of cycles to failure and maximum tangential stress or shear deformation, thereby predicting the lifetime of the test object.

2. The method of claim 1, wherein the predetermined relationship between ISG reaction value, amplitude of tangential stress or shear deformation and number of loading cycles is determined from calibration experiments, each calibration experiment being conducted with an ISG attached to a calibration specimen, the surface of each ISG comprising a reaction sensitive material, the surface of the reaction sensitive material indicating a reaction due to a change in grain size and number of grains per unit area at the surface of the reaction sensitive material upon deformation of the calibration specimen.

3. The method of claim 1, wherein the relationship between number of cycles to failure and maximum tangential stress or shear deformation is determined from fatigue experiments, each fatigue experiment being conducted with an ISG attached to a fatigue test specimen, the surface of each ISG comprising a reaction sensitive material, the surface of the reaction sensitive material indicating a reaction due to a change in grain size and number of grains per unit area at the surface of the reaction sensitive material upon deformation of the fatigue test specimen.

4. A method for using an integral strain gauge (ISG) to predict the lifetime of a test object, the surface of the ISG comprising a reaction sensitive material, the surface of the reaction sensitive material indicating a reaction due to a change in grain size and number of grains per unit area at the surface of the reaction sensitive material upon deformation of the attached test object, the method comprising the steps of:
   a) attaching the ISG to the surface of the test object;
   b) applying a plurality of loading cycles to the test object, the number of loading cycles being known and the loading cycles inducing cyclic strain in the test object, with the amplitude of the loading induced strain being constant;
   c) reading a reaction value on the surface of the ISG attached to the test object;
   d) determining the maximum stress or loading induced strain during step b) from the ISG reaction value of step c) and a predetermined relationship between ISG reaction value, amplitude of tangential stress or shear deformation and number of loading cycles;
   e) determining the number of cycles to failure from the maximum stress or loading induced strain determined in step d) and a predetermined relationship between number of cycles to failure and maximum tangential stress or shear deformation, thereby predicting the lifetime of the test object wherein the predetermined relationship between ISG reaction value, amplitude of tangential stress or shear deformation and number of loading cycles is determined from calibration experiments, each calibration experiment being conducted with an ISG attached to a calibration specimen, the calibration specimen comprising an inner elastic rod and an outer working shell of an amorphous material, the inner rod and the outer shell being attached to each other.

5. A method for using an integral strain gauge (ISG) to predict the lifetime of a test object, the surface of the ISG comprising a reaction sensitive material, the surface of the reaction sensitive material indicating a reaction due to a change in grain size and number of grains per unit area at the surface of the reaction sensitive material upon deformation of the attached test object, the method comprising the steps of:
   a) attaching the ISG to the surface of the test object;
   b) applying cyclic loading to the test object in a plurality of stages, each stage inducing cyclic strain in the test object, the amplitude of the loading induced strain varying according to a set block of loads;
   c) reading a reaction value on the surface of the ISG attached to the test object;
   d) computing the number of loading cycles in step b);
   e) determining an equivalent maximum loading induced strain during step b) from the ISG reaction value determined in step c), the number of loading cycles computed in step d) and a predetermined relationship between ISG reaction value, amplitude of tangential stress or shear deformation and number of loading cycles;
   f) determining the number of cycles to failure from the equivalent maximum loading induced strain determined in step e) and a predetermined relationship between number of cycles to failure and maximum tangential stress or shear deformation, thereby predicting the lifetime of the test object.

6. The method of claim 5, wherein the predetermined relationship between number of cycles to failure and maximum tangential stress or shear deformation is determined from fatigue experiments in which cyclic loading is applied to the fatigue test specimens according to the set block of loads of step b).

\* \* \* \* \*